US008658711B2

(12) United States Patent
Shreiber et al.

(10) Patent No.: US 8,658,711 B2
(45) Date of Patent: Feb. 25, 2014

(54) PROCESS FOR THE SYNTHESIS OF METHACRYLATE-DERIVATIZED TYPE-1 COLLAGEN AND DERIVATIVES THEREOF

(75) Inventors: David Shreiber, Whitehouse Station, NJ (US); Ian Gaudet, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/249,134

(22) Filed: Sep. 29, 2011

(65) Prior Publication Data
US 2012/0220691 A1    Aug. 30, 2012

Related U.S. Application Data

(60) Provisional application No. 61/387,749, filed on Sep. 29, 2010.

(51) Int. Cl.
*A61F 2/00*        (2006.01)
(52) U.S. Cl.
USPC ............................ 523/113; 424/487; 536/55.1
(58) Field of Classification Search
USPC ....... 523/113; 424/487; 536/55.1; 514/12, 21
See application file for complete search history.

(56) References Cited

U.S. PATENT DOCUMENTS

| | | | | | |
|---|---|---|---|---|---|
| 4,452,925 | A | * | 6/1984 | Kuzma et al. | 523/106 |
| 6,117,979 | A | * | 9/2000 | Hendriks et al. | 530/356 |
| 2005/0020506 | A1 | * | 1/2005 | Drapeau et al. | 514/21 |
| 2009/0238875 | A1 | * | 9/2009 | Noh et al. | 424/487 |

OTHER PUBLICATIONS

Brinkman et al., "Photo-cross-linking of Type I Collagen Gels in the Presence of Smooth Muscle Cells: Mechanical Properties, Cell Viability and Function," Biomacromols., 4(4), 890-895, 2003 Jul.-Aug. Abstract only.
Bryant et al., "Encapsulating Chondrocytes in Degrading PEG Hydrogels With High Modulus: Engineering Gel Structural Changes to Facilitate Cartilagi-nous Tissue Production," Biotech. Bioeng., 86(7), 747-55, Jun. 30, 2004. Abstract only.
Cen et al., "Collagen Tissue Engineering: Development of Novel Biomaterials and Applications," Ped. Res., 63(5) 492-496, May 2008. Abstract only.
Cheung et al., "Mechanism of Crosslinking of Proteins by Glutaraldehyde III. Reaction with Collagen in Tissues," Connect. Tiss. Res., 13(2), 109-115, 1985. Abstract only.
Cheung, HY, et al., "A Critical Review on Polymer-Based Bio-Engineered Materials for Scaffold Development," Compos. Part B-Eng., 38(3), 291-300, 2007.
Damink et al., "In Vitro Degradation of Dermal Sheep Collagen Cross-Linked Using a Water-Soluble Carbodiimide," Biomater., 17(7), 679-684, Apr. 1996. Abstract only.
Discher et al., "Matrix Elasticity Directs Stem Cell Lineage Specification," Cell, 126, 677-689, Aug. 25, 2006.

(Continued)

*Primary Examiner* — James J Seidleck
*Assistant Examiner* — Peter A Salamon
(74) *Attorney, Agent, or Firm* — Fox Rothschild LLP

(57) ABSTRACT

Methods for synthesizing a methacrylate-derivatized type-I collagen in which methacrylic acid is reacted with a carboxylic acid activating reagent in the presence of a carbodiimide to form a methacrylic acid with an activated carboxylic acid group, which is then reacted with free amino groups on type-I collagen to form a collagen methacrylamide. Methacrylate-derivatized collagen, cross-linked collagens formed therefrom and products containing the cross-linked collagen are also disclosed.

23 Claims, 6 Drawing Sheets

(56) References Cited

OTHER PUBLICATIONS

Discher et al., "Tissue Cells Feel and Respond to the Stiffness of Their Substrate." Science, 310(5751), 1139-1143, Nov. 18, 2005. Abstract only.

Dong et al., "Photomediated Crosslinking of C6-Cinnamate Derivatized Type I Collagen," Biomater., 26(18), 4041-4049, Jun. 2005. Abstract only.

Ibusuki et al., "Photochemically Cross-Linked Collagen Gels as Three-Dimensional Scaffolds for Tissue Engineering," Tiss. Eng., 13(8), 1995-2001, Aug. 2007. Abstract only.

Jen et al., "Review: Hydrogels for Cell Immobilization," Biotech. Bioeng., 50(4), 357-364, May 20, 1996. Abstract only.

Lee, et al., "Hydrogels for Tissue Engineering," Chem. Rev., 101(7), 1869-1879, 2001. Abstract only.

Levenberg et al., "Cell-Scaffold Mechanical Interplay Within Engineered Tissue," Semin. Cell Dev. Bio., 20(6), 656- 64, Aug. 2009. Abstract only.

Nicodemus et al., "Cell Encapsulation in Biodegradable Hydrogels for Tissue Engineering Applications," Tissue Eng. Part B-Rev., 14(2), 149-165, Jun. 2008. Abstract only.

O'Connor et al., "Review: Ex vivo Engineering of Living Tissues with Adult Stem Cells," Tiss. Eng., 12(11), 3007-3019, Nov. 2006 Abstract only.

Park et al., "Characterization of porous collagen/hyaluronic acid scaffold modified by 1-ethyl-3-(3-dimethylaminopropyl)carbodiimide cross-linking," Biomaterials, 23(4), 1205-1212, Feb. 2002 Abstract only.

Poshusta et al., "Photopolymerized Biomaterials for Application in the Temporo-mandibular Joint," Cells Tiss. Orgs., 169(3), 272-278, 2001. Abstract only.

Rehfeldt et al., "Cell Res-ponses to the Mechanochemical Microenvironment—Implications for Regenerative Medicine and Drug Delivery," Adv. Drug Del. Rev., 59(13), 1329-1339, Nov. 2007 Abstract only.

Sheu et al., "Characterization of Collagen Gel Solutions and Collagen Matrices for Cell Culture," Biomater., 22(13), 1713-1719, Jul. 2001 Abstract only.

Walton et al., "Influence of Telopeptides, Fibrils and Crosslinking on Physicochemical Properties of Type I Collagen Films," J. Mater. Sci.-Maters. in Med., 21(2), 451-461, Feb. 2010 Abstract only.

Weadock et al., "Effect of Physical Crosslinking Methods on Collagen-Fiber Durability in Proteolytic Solutions," J. Biomed. Mater. Res., 32(2), 221-226, Oct. 1996 Abstract only.

Yang et al., "Mechanical Properties of Native and Cross-Linked Type I Collagen Fibrils," Biophys. J., 94(6), 2204-2211, Mar. 2008 Abstract only.

\* cited by examiner

PROCESS FOR THE SYNTHESIS OF METHACRYLATE-DERIVATIZED TYPE-1 COLLAGEN AND DERIVATIVES THEREOF

CROSS-REFERENCE TO RELATED APPLICATIONS

This application claims priority benefit under 35 U.S.C. §119(e) of U.S. Provisional Application No. 61/387,749 filed Sep. 29, 2010, the disclosure of which is incorporated herein by reference in its entirety.

BACKGROUND OF THE INVENTION

The present invention relates to a novel process for creating a robust, photocross-linkable collagen, and a process for creating a collagen and PEG-based hybrid biomaterial that allows for mechanical and biofunctional modulation using the application of light and a suitable photo-initiator.

Generally, collagen is a group of naturally occurring proteins found in animals, especially in the flesh and connective tissues of mammals. It is the main component of connective tissue, and is the most abundant protein in mammals, making up about 25% to 35% of the whole-body protein content. Collagen, in the form of elongated fibrils, is mostly found in fibrous tissues such as tendon, ligament and skin, and is also abundant in cornea, cartilage, bone, blood vessels, the gut, and intervertebral disc.

Type-I collagen is the major collagen of tendon and bone, but it is also the predominant in lung, skin, dentin, heart valves, fascia, scar tissue, cornea, and liver. Type I collagen is essential for the tensile strength of bone. It is the final amount and distribution of these collagen fibers that will determine the size, shape, and ultimate density of the bone.

Polyethylene glycol ("PEG") has been used in medical implants and pharmaceuticals in a number of formulations for decades. In 1995, PEG was modified by adding reactive acrylate groups to the end of the PEG macromer to form PEG diacrylate, which was then photo-polymerized and used to form synthetic hydrogel matrices in which encapsulated cells could be grown.

Hydrogels are semi-solid structures comprising networks of water-insoluble polymers surrounded by water (Lee, et al., "Hydrogels for Tissue Engineering," *Chem. Rev.*, 101(7), 1869-1880 (2001)). They are attractive materials for use as tissue engineering scaffolds, particularly those made from materials that can polymerize in an aqueous environment that have potential to be injected into a defect or wound, and then polymerized to provide a stable matrix for cellular growth, remodeling, and regeneration into functional tissues (Nicodemus et al., "Cell Encapsulation in Biodegradable Hydrogels for Tissue Engineering Applications," *Tissue Eng. Part B-Rev.*, 14(2), 149-165 (2008); Bryant et al., "Encapsulating Chondrocytes in Degrading PEG Hydrogels With High Modulus: Engineering Gel Structural Changes to Facilitate Cartilaginous Tissue Production," *Biotech. Bioeng.*, 86(7), 747-55 (2004); Jen et al., "Review: Hydrogels for Cell Immobilization," *Biotech. Bioeng.*, 50(4), 357-364 (1996).) Natural hydrogels from proteins such as collagen, are both cytocompatible and highly biofunctional, but have somewhat constrained material properties and inherentability in composition due to their biological origin, making them more difficult to work with from an engineering viewpoint. (Cheung et al., "Mechanism of Cross-Linking of Proteins by Glutaraldehyde 0.3. Reaction with Collagen in Tissues," *Connect. Tiss. Res.*, 13(2), 109-115 (1985); Cen et al., "Collagen Tissue Engineering: Develop-ment of Novel Biomaterials and Applications," *Ped. Res.*, 63(5)492-496 (2008); Yang et al., "Mechanical Properties of Native and Cross-Linked Type I Collagen Fibrils," *Biophys. J.*, 94(6), 2204-2211 (2008).)

In recent years, the mechanical microenvironment has been elucidated as a potent modulator of cellular behavior and thus has been of great interest in designing scaffolds for tissue engineering. (Levenberg et al., "Cell-Scaffold Mechanical Interplay Within Engineered Tissue,"*Sem. Cell Dev. Bio.*, 20(6), 656-664 (2009); Discher et al., Tissue Cells Feel and Respond to the Stiffness of Their Substrate, *Science*, 310 (5751), 1139-1143 (2005); Rehfeldt et al., "Cell Responses to the Mechanochemical Microenvironment—Implications for Regenerative Medicine and Drug Delivery," *Adv. Drug Del. Rev.*, 59(13), 1329-1339 (2007).) In particular, stem cell-based tissue regeneration has shown scaffold mechanics to be of crucial importance in guiding and maintaining differentiation pathways. (O'Connor et al., "Review: Ex vivo Engineering of Living Tissues with Adult Stem Cells," *Tiss. Eng.*, 12(11), 3007-3019 (2006); Discher et al., "Matrix Elasticity Effects on Cardiomyocytes and Stem Cells: Similarities, Differences and Therapeutic Implications," *Biorheol.*, 45(1-2), 54 (2008); Discher et al., "Matrix Elasticity Directs Stem Cell Lineage Specification," *Biophys. J.*, 32a-32a (2007).) Synthetic scaffolds are increasingly popular, partly due to the ease with which their mechanical properties—as well as other characteristics—can be modulated. Natural materials such as collagen, while having the benefits of bio-activity, biodegradability, and innate adhesiveness, have been criticized for the limited control of their mechanical properties. (Lau et al., A Critical Review on Polymer-Based Bio-Engineered Materials for Scaffold Development," *Compos. Part B-Eng.*, 38(3), 291-300 (2007).)

Hybrid materials, which contain a mixture of biomaterials and synthetic components, are becoming popular as tissue engineering matrices due to the combination of their respective advantages. Several groups have used combinations of natural and synthetic materials to optimize and tailor the properties of tissue engineering scaffolds to the particular application. However, simply combining biomaterials with synthetics has limitations, due to the drawbacks of having both materials everywhere within the scaffold. In the case of PEG, this could prevent cell attachment.

Other approaches using hybrid materials involve using collagen as a base material, and admixing additional natural or synthetic components such as hyaluronic acid and polyethylene oxide to form interpenetrating networks. A major drawback to this system is again there is little control over where materials interact, and it may be hard to determine with which material cells might interface due to the presence of two independent matrices.

Previous attempts at modifying collagen's material properties have presented significant challenges. Although chemical cross-linking using glutaraldehyde provides significant increases in mechanical strength, it is highly cytotoxic. More cytocompatible cross-linking compounds, such as genipin, allow cross-linking in the presence of cells, although the degree of cross-linking is limited and localization of cross-linking is difficult due to diffusion of chemical agents through the hydrogel. Enzymes, such as transglutaminases, are non-cytotoxic but are prohibitively expensive and are also subject to uncontrolled diffusion. Other approaches, such as exposure to UV light are either cytotoxic, in the case of UVC, or minimally effective and slow, as with UVA exposure. Collagen has been reportedly directly crosslinked using UV light with riboflavin as a photosensitizing agent, although numerous tests have shown this method does not significantly change the mechanical properties, and is quite cytotoxic as well.

Photocrosslinking of collagen has been pursued in a variety of ways. UV irradiation in the presence of flavin mononucleotide produced only minimal changes in mechanical properties, and only when crosslinking was done prior to self-assembly. (Ibusuki et al., "Photochemically Cross-Linked Collagen Gels as Three-Dimensional Scaffolds for Tissue Engineering," *Tiss. Eng.*, 13(8), 1995-2001 (2007).) Collagen has also been modified via addition of photosensitive cinnamate groups, although the wavelength needed to crosslink is cytotoxic which prevents crosslinking in the presence of cells. (Dong et al., Photomediated Cros slinking of C6-Cinnamate Derivatized Type I Collagen," *Biomater.*, 26(18), 4041-4049 (2005).) Other approaches first modified collagen with either acrylate or methacrylate groups prior to photoinitiator-activated cross-linking. (Poshusta et al., "Photopolymerized Biomaterials for Application in the Temporo-mandibular Joint," *Cells Tiss. Orgs.*, 169(3), 272-278 (2001); Brinkman et al., "Photo-cross-linking of Type I Collagen Gels in the Presence of Smooth Muscle Cells: Mechanical Properties, Cell Viability and Function," *Biomacromols.*, 4(4), 890-895 (2003).) However, reaction conditions in these methods resulted in either unwanted gelation during reaction or partial denaturation of the collagen, which, while producing a useful photosensitive material, resulted in loss of the collagen to self-assemble into fibrils similar to native collagen.

More recently, there have been attempts made to modify collagen with photoactive groups such that light, in conjunction with a photoinitiator, might be used to significantly produce material changes spatially and in a cytocompatible manner. However, these approaches appear to have the common problem that the reaction conditions under which the collagen is modified are too harsh to preserve the complex tertiary structure, the result of which is that the collagen becomes partially denatured and is no longer able to spontaneously self-assemble.

Several groups have used collagen gels as matrices for stem and neural precursor cell-based therapies in central nervous system ("CNS") injury models. While their results show that collagen gels are suitable for supporting both stem cell proliferation and differentiation into neural tissues, prior to the development of the instant invention these materials lacked the ability to produce localized, controlled heterogeneity, which may be necessary to completely regenerate damaged tissues and restore function to pre-injury levels.

SUMMARY OF THE INVENTION

The present invention provides a photosensitive material based on type-I collagen to modulate mechanical properties via the application of light. A method is provided for the synthesis of collagen methacrylamide (CMA) in which the free amines are derivatized with reactive methacrylate groups without significantly altering the structural and functional properties that make type I collagen an attractive and useful scaffold material. The CMA prepared by the method of the present invention is able to self-assemble from a liquid macromer solution into a fibrillar hydrogel at physiological pH and temperature, with similar assembly kinetics and resultant structure as compared to native type I collagen.

Therefore, according to one aspect of the present invention, a method of synthesizing a methacrylate-derivatized type-I collagen is provided, in which methacrylic acid os reacted with a carboxylic acid activating reagent in the presence of a carbodiimide to form a methacrylic acid with an activated carboxylic acid group; which is then reacted with the free amino groups on type-I collagen to form a collagen methacrylamide. In one embodiment, the carbodiimide is selected from 1-ethyl-3-(3-dimethylamino-propyl) carbodiimide (EDC), N,N'-dicyclohexyl-carbodiimide (DHC), N,N'-diisopropylcarbodiimide (DIC), 1-(3-dimethylaminopropyl)-3-ethyl carbodiimide hydrochloride, N-cyclohexyl-N'-(2'-morpholinoethyl) carbodiimide-metho-p-toluene sulfonate, N-benzyl-N'-3'-dimethylaminopropyl-carbodiimide hydrochloride, 1-ethyl-3-(3-dimethylaminopropyl)carbodiimide methiodide and N-ethylcarbodiimide hydrochloride.

In another embodiment the carboxylic acid activating reagent is selected from N-hydroxysuccinimide (NHS), N-hydroxysulfosuccinimide (Sulfo-NHS), Hydroxybenzotriazole (HOBt), 1-Hydroxy-7-azabenzotriazole (HOAt) and pentafluorophenol.

Collagen methacrylamide prepared by the method of the present invention retains the ability to self-assemble unlike the collagen methacrylamide prepared by prior art methods. Accordingly, another aspect of the present invention provides collagen methacrylamide prepared by the method of the present invention. Typically, between about 5 and about 25% of the collagen free amino groups on the collagen methacrylamide are acrylate-functionalized.

The present invention also provides a method by which the collagen methacrylamide of the present invention can be further functionalized with methacrylate groups at free carboxylic acid groups on the collagen. Methods according to this aspect of the present invention further include the steps of removing excess reagents from the collagen methacrylamide; reacting free carboxylic acid groups on the collagen methacrylamide with a carboxylic acid activating reagent in the presence of a carbodiimide to form a collagen methacrylamide with activated carboxylic acid groups; and reacting the activated carboxylic acid groups on said collagen methacrylamide with an amino-(lower alkyl)-methacrylate in the presence of a carbodiimide to form a collagen methacrylamide amidoalkylmethacrylate. The lower alkyl group can contain from one to six carbon atoms and is preferably an ethyl group.

The acrylate groups of the collagen methacrylamides of the present invention are photo-cross-linked by conventional means using UV light and a photosensitizer. Accordingly, the present invention also provides cross-linked collagens prepared from the collagen methacrylamides of the present invention. Cross-linked collagen methacrylamides are also provided on which a portion of the acrylate functional groups are cross-linked by conventional means with a poly(alkylene oxide)dimethacrylate such as poly(ethylene glycol) dimethacrylate.

The cross-linked collagens of the present invention are provided in lyophilized form and also as hydrogels. The cross-linked collagens can be used to improve the performance of products typically made from collagen, such as scaffolds for tissue engineering, implantable medical devices, wound dressings and tissue replacement materials for cosmetic or reconstructive surgery. Tissue replacement materials formed from the cross-linked collagen of the present invention can be configured as skin, bone tissue, blood vessels, fascia, connective tissue cartilaginous tissue, such as spinal discs, knee menisci, ligaments, tendons, etc., and the like. Dermal filler, bone filler and artificial skin can also be prepared from the cross-linked collagen of the present invention.

There products can be formed from the cross-linked collagen of the present invention prior to use or the products may be formed from the collagen methacrylamides of the present invention and cross-linked in situ. The present invention therefore also provides scaffolds for tissue engineering, implantable medical devices, wound dressings and tissue replacement materials for cosmetic or reconstructive surgery formed from the collagen methacrylamides of the present invention. Tissue replacement materials are also provided that are formed from the collagen methacrylamides of the present invention and configured as skin, bone tissue, blood vessels, fascia, connective tissue cartilaginous tissue, such as spinal discs, knee menisci, ligaments, tendons, etc., and the like. Dermal filler, bone filler and artificial skin are also provided, prepared from the collagen methacrylamides of the present invention.

When cross-linked in situ, the photocross-linking conditions can be selected to modulate the mechanical properties of the collagen product. In one embodiment an implantable collagen methacrylamide material is provided that is soft and flexible to permit suturing and then stiffened to a desired degree of stiffness by the degree to which it is subsequently photocross-linked.

A more complete appreciation of the invention and many other intended advantages can be readily obtained by reference to the following detailed description of the preferred embodiment and claims, which disclose the principles of the invention and the best modes which are presently contemplated for carrying them out.

DETAILED DESCRIPTION OF THE INVENTION

The instant invention provides a method for the addition of photosensitive methacrylate groups to collagen that minimizes denaturation of the collagen protein and retains its ability to self-assemble into a biocompatible and bioactive hydrogel scaffold. This material provides a stable environment into which localized modifications can be made to the material properties of the hydrogel scaffold.

The instant invention provides a photosensitive material based on type-I collagen methacrylamide (CMA) to modulate mechanical properties via the application of light. The method to synthesize collagen methacrylamide allows for the derivatization of free amines with reactive methacrylate groups without significantly altering the structural and functional properties that make type-I collagen an attractive and useful scaffold material. CMA is able to self-assemble from a liquid macromer solution into a fibrillar hydrogel at physiological pH and temperature, with similar assembly kinetics and resultant structure as compared to native type-I collagen.

Figure 1:
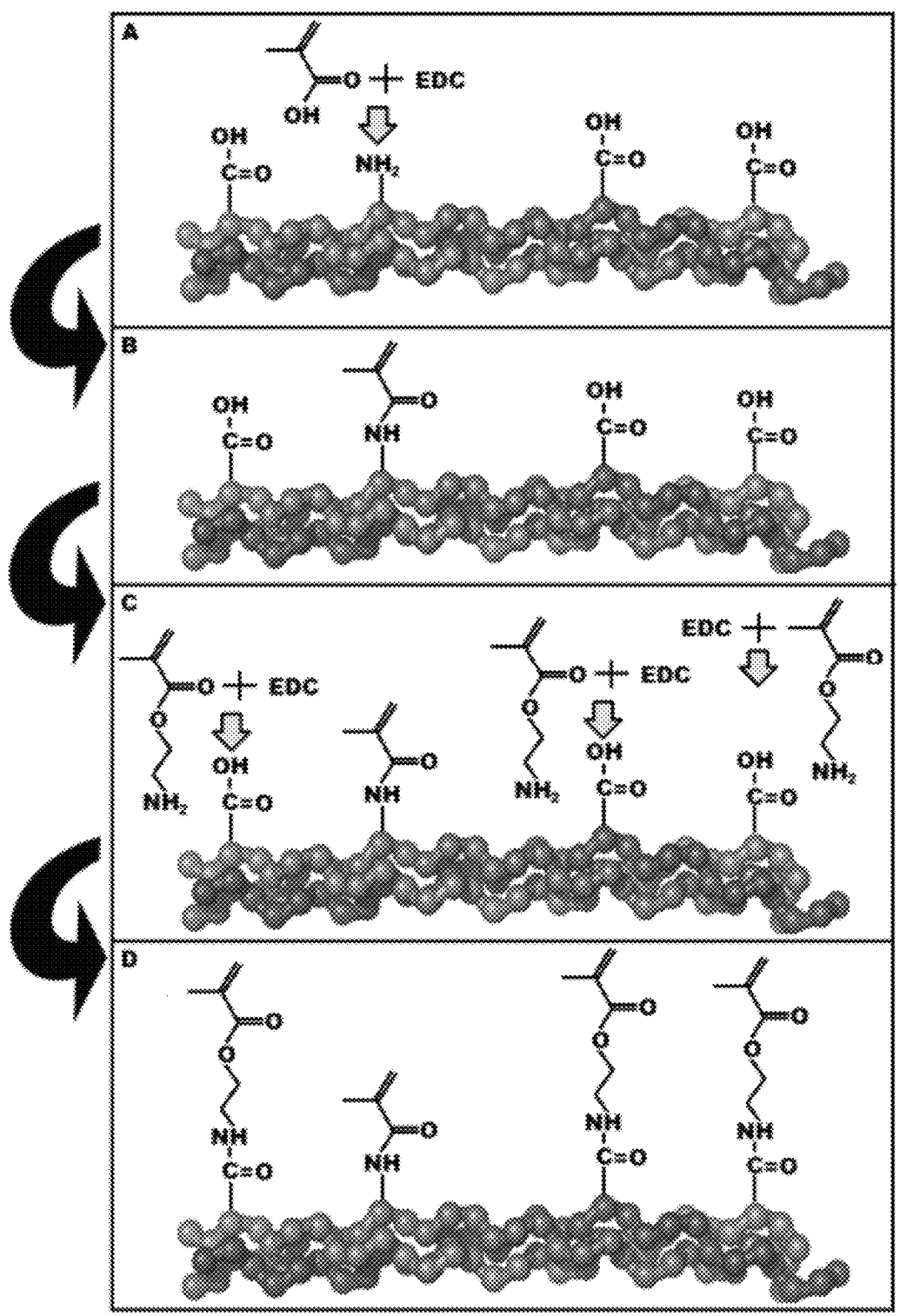
FIG. 1: depicts the synthesis method for the preparation of collagen methacrylamide (CMA) and the subsequent preparation of collagen methacrylamide amidoethylmethacrylate.
Figure 2:
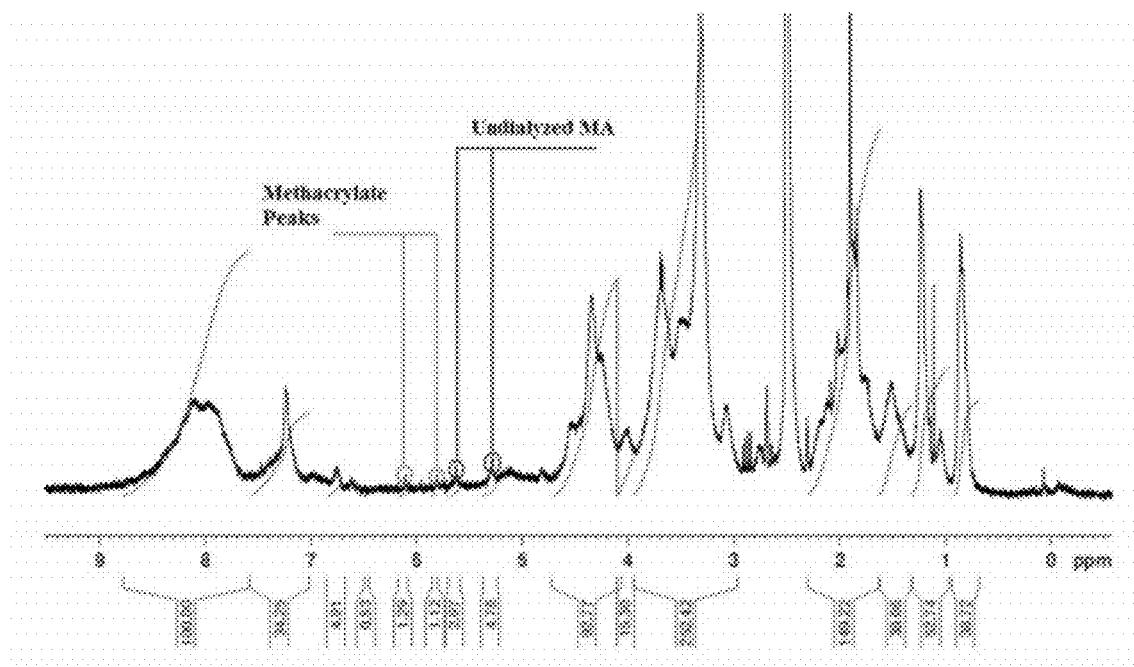
FIG. 2 depicts the $H^1$ NMR Spectrum of CMA.
Figure 3:
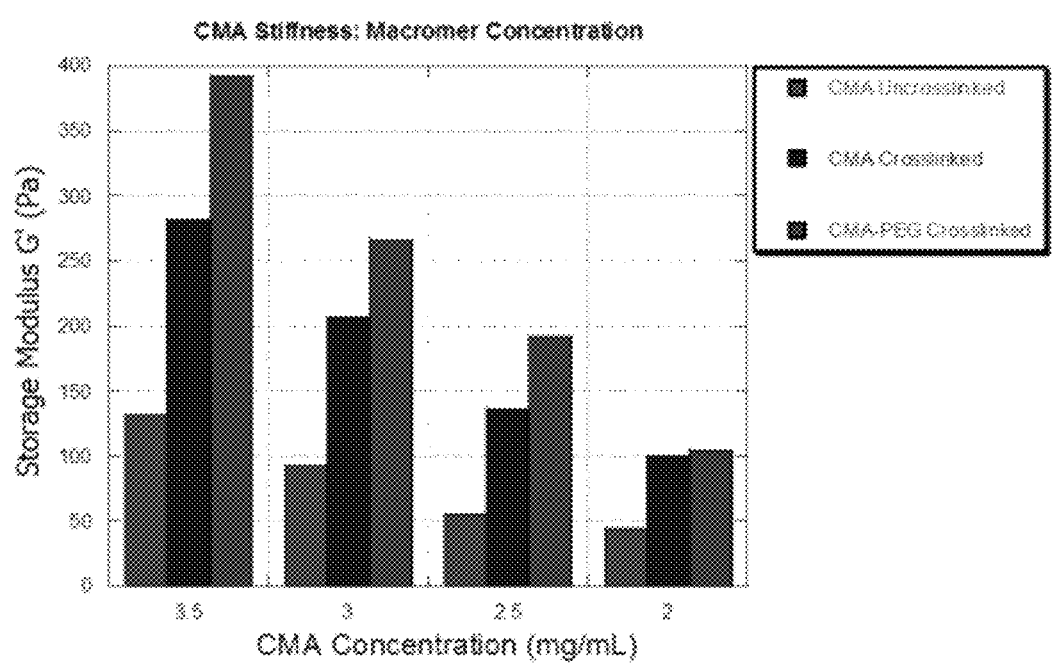
FIG. 3 depicts the G' (Pa) of CMA/PEG 258 DA Hydrogels UV crosslinked with I2959.

Collagen methacrylamides according to the present invention are prepared by the method depicted in FIG. 1. Methacrylic acid is reacted with a carboxylic acid activating reagent in the presence of a carbodiimide to form a methacrylic acid with an activated carboxylic acid group. Essentially any of the well-known carboxylic acid activating reagents can be used, examples of which include N-hydroxysuccinimide (NHS), N-hydroxysulfosuccinimide (Sulfo-NHS), Hydroxybenzotriazole (HOBt), 1-Hydroxy-7-azabenzotriazole (HOAt) and pentafluorophenol. In the method depicted in FIG. 1, NHS was used.

Likewise, essentially any carbodiimide capable of activating carboxylic acids toward amide formation can be used, examples of which include 1-ethyl-3-(3-dimethylamino-propyl) carbodiimide (EDC), N,N'-dicyclohexyl-carbodiimide (DHC), N,N'-diisopropylcarbodiimide (DIC), 1-(3-dimethylaminopropyl)-3-ethyl carbodiimide hydrochloride, N-cyclohexyl-N'-(2'-morpholinoethyl) carbodiimide-metho-p-toluene sulfonate, N-benzyl-N'-3'-dimethylamino-propyl-carbodiimide hydrochloride, 1-ethyl-3-(3-dimethylaminopropyl) carbodiimide meth-iodide and N-ethylcarbodiimide hydrochloride. In the method depicted in FIG. 1, EDC was used.

The activated methacrylic acid is then reacted with the free amino groups on type-I collagen to form a collagen methacrylamide. As demonstrated in the examples, the collagen methacrylamide is purified by conventional means, for example, by dialysis.

Typically, between about 5 and about 25% of the collagen free amino groups on the collagen methacrylamide are acrylate-functionalized. In another embodiment between about 10 and about 20% inclusive, of the collagen free amino groups on the collagen methacrylamide are acrylate-functionalized.

The present invention also provides a method by which the collagen methacrylamide of the present invention can be further functionalized with methacrylate groups at free carboxylic acid groups on the collagen. Methods according to this aspect of the present invention activate free carboxylic acid groups on the collagen methacrylamide essentially the same way the acrylic acid carboxylic acid groups were activated, i.e., with a carboxylic acid activating reagent in the presence of a carbodiimide to form a collagen methacrylamide with activated carboxylic acid groups. The same activating reagents and carbodiimides can be used. The activated carboxylic acid groups are then reacted with an amino-(lower alkyl)-methacrylate to form a collagen methacrylamide amidoalkylmethacrylate. The lower alkyl group can contain from one to six carbon atoms and is preferably an ethyl group.

As depicted in the Examples, the acrylate groups of the collagen methacrylamides of the present invention are photocross-linked by conventional means using UV light and a photo-sensitizer. In one embodiment, portion of the acrylate functional groups are cross-linked by conventional means with a poly(alkylene oxide)dimethacrylate such as poly(ethylene glycol) dimethacrylate. Poly(ethylene glycols) with a molecular weight between about 1,000 and 2,000 are preferred and are employed in a concentration between about 0.01 and about 1.0% w/v, and more preferably between about 0.05 and about 0.50% w/v.

The cross-linked collagens of the present invention may be worked up by conventional means in lyophilized form and also as hydrogels. The concentration of the collagen methacryl-amide in the hydrogel can be selected to obtain a desired stiffness either before or after the collagen is cross-linked. Concentrations between about 1.0 and about 5.0 mg/mL in the hydrogel can be used. In one embodiment the concentration is between about 2 and 3.5 mg/mL.

The cross-linked collagens can be used to improve the performance of products typically made from collagen, such as scaffolds for tissue engineering, implantable medical devices, wound dressings and tissue replacement materials for cosmetic or reconstruct-ive surgery. Tissue replacement materials formed from the cross-linked collagen of the present invention can be configured as skin, bone tissue, blood vessels, fascia, connective tissue cartil-aginous tissue, such as spinal discs, knee menisci, ligaments, tendons, etc., and the like. Dermal filler, bone filler and artificial skin can also be prepared from the cross-linked collagen of the present invention.

There products can be formed from the cross-linked collagen of the present invention prior to use or the products may be formed from the collagen methacrylamides of the present invention and cross-linked in situ. The present invention therefore also provides scaffolds for tissue engineering, implantable medical devices, wound dressings and tissue replacement materials for cosmetic or reconstructive surgery formed from the collagen methacrylamides of the present invention. Tissue replacement materials are also provided that are formed from the collagen methacrylamides of the present invention and configured as skin, bone tissue, blood vessels, fascia, connective tissue cartilaginous tissue, such as spinal discs, knee menisci, ligaments, tendons, etc., and the like. Dermal filler, bone filler and artificial skin are also provided, prepared from the collagen methacrylamides of the present invention.

When cross-linked in situ, the photocross-linking conditions can be selected to modulate the mechanical properties of the collagen product. In one embodiment an implantable collagen methacrylamide material is provided that is soft and flexible to permit suturing and then stiffened to a desired degree of stiffness by the degree to which it is subsequently photocross-linked.

One advantage of the collagen methacrylamide of the present invention is that the derivatization reaction conditions preserve the ability of collagen to self-assemble, while allowing significant spatially controllable modulation of the material properties in the presence of live cells. Consequently, mechanically tunable collagen hydrogels can be used in a broad range of applications where heterogeneous control of the material properties is desired. One major advantage of collagen is its ability to self-assemble, which can allow the material to be injected into a defect of almost any geometry with minimal invasion, and then automatically become a solid to provide a stable matrix. Crosslinking can then be accurately introduced into any spatial pattern where light application is accessible. As the photocrosslinking process is cytocompatible, cells in the liquid scaffold can be injected into a defect, followed by scaffold modulation in situ via photocross-linking to create an optimal environment for tissue regeneration that is customizable to an individual patient.

Accordingly, in another embodiment of the present invention, the collagen methacryl-amide hydrogels of the present invention may be seeded with stem cells or other cells for tissue regeneration. In another embodiment, the lyophilized collagen methacrylamides or the collagen methacrylamide hydrogels of the present invention are provided with biologically active compounds that promote tissue growth within the scaffold, examples of which include cell attachment mediators, such as the peptide containing variations of the "RGD" integrin binding sequence known to affect cellular attachment, biologically active ligands, and substances that enhance or exclude particular varieties of cellular or tissue ingrowth. Such substances include, for example, osteoinductive substances, such as bone morphogenic proteins (BMP), epidermal growth factor (EGF), fibroblast growth factor (FGF), platelet-derived growth factor (PDGF), insulin-like growth factor (IGF-I and II), TGF-.beta. and the like.

In another embodiment, the lyophilized collagen methacrylamides or the collagen methacrylamide hydrogels of the present invention are provided with therapeutic agents that are beneficial to the end-use application of the collagen. Hydrogel scaffolds allow for controlled release of therapeutic agents. Examples of the therapeutic agents include, but are not limited to, growth factors, vitamins, minerals, natural oils, phytochemicals, enzymes, anti-oxidants, anti-ageing agents, alpha hydroxy acids, glycolic acid, salicylic acid, antibiotics, antimicrobials, anti-tumor agents, anti-inflammatory agents, non-steroidal anti-inflammatory agents (NSAIDS), neurotropic agents, and the like.

Specific examples of suitable therapeutic agents include, but are not limited to, acyclovir, cephradine, malfalen, procaine, ephedrine, adriomycin, daunomycin, plumbagin, atropine, guanine, digoxin, quinidine, biologically active peptides, chlorin $e_6$, cephalothin, proline and proline analogues such as cis-hydroxy-L-proline, penicillin V, aspirin, ibuprofen, steroids, nicotinic acid, chemodeoxycholic acid, chlorambucil, and the like.

In the instant invention, the release rate of the therapeutic agent can be controlled locally by increasing the cross-linking density and hence the porosity of the scaffold. The scaffolds are shaped into articles for tissue engineering and tissue guided regeneration applications, including reconstructive surgery. The scaffolds may also be molded to form external scaffolding for the support of in vitro culturing of cells for the creation of external support organs.

The scaffold functions to mimic the extracellular matrices (ECM) of the body. The scaffold serves as both a physical support and an adhesive substrate for isolated cells during in vitro culture and subsequent implantation. As the transplanted cell populations grow and the cells function normally, they begin to secrete their own ECM support. The scaffold is designed to degrade as the need for an artificial support diminishes.

In the reconstruction of structural tissues like cartilage and bone, tissue shape is integral to function, requiring the molding of the scaffold into articles of varying thickness and shape. Any crevices, apertures or refinements desired in the three-dimensional structure can be created by removing portions with scissors, a scalpel, a laser beam or any other cutting instrument. The collagen methacrylamides of the present invention can be molded and shaped prior to cross-linking and stiffened after the desired shape is achieved, either ex vivo or in situ. Scaffold applications include the regeneration of tissues such as nervous, musculoskeletal, cartilaginous, tendenous, hepatic, pancreatic, ocular, integumenary, arteriovenous, urinary or any other tissue forming solid or hollow organs.

The scaffold may also be used in transplantation as a matrix for dissociated cells such as chondrocytes or hepatocytes to create a three-dimensional tissue or organ. Any type of cell can be added to the scaffold for culturing and possible implantation, including cells of the muscular and skeletal systems, such as chondrocytes, fibroblasts, muscle cells and osteocytes, parenchymal cells such as hepatocytes, pancreatic cells (including Islet cells), cells of intestinal origin, and other cells such as nerve cells and skin cells, either as obtained from donors, from established cell culture lines, or even before or after genetic engineering. Pieces of tissue can also be used, which may provide a number of different cell types in the same structure.

The cells are obtained from a suitable donor, or the patient into which they are to be implanted, dissociated using standard techniques and seeded onto and into scaffold, either before or after cross-linking. In vitro culturing optionally may be performed prior to implantation. Alternatively, the scaffold is implanted, allowed to vascularize, then cells are injected into the scaffold. In yet another alternative method, a scaffold is implanted containing growth factors that recruit the ingrowth of surrounding tissue. Methods and reagents for culturing cells in vitro and implantation of a tissue scaffold are known to those skilled in the art.

One clinical application is in a central nervous system (CNS) injury. The native tissue in the CNS has mechanical properties similar to those of collagen gels, and neural tissue behavior has been shown to be highly responsive to changes in stiffness. Moreover, CNS injuries can result in lesion cavities with non-uniform geometries that are not amenable to solid scaffold implantation without the risk of additional damage to the injury site.

It has been demonstrated that the growth of regenerating neurites from dorsal root ganglia is directed and enhanced down gradients of compliance. However, the scope and profile of these gradients can be limited by the tolerable concentrations of the soluble cross-linker used, and by dimensional constraints associated with maintaining laminar flow regimes in microfluidic networks. Functionality and improved versatility of durotactic gradients formed with this novel, photoreactive hybrid material for regenerating axons is demonstrated. Moreover, guidance of cell types other than neurons, such as astrocytes, is shown to cause a secondary alignment of neurons. Taking advantage of this allows reorganization of the glial scar present in many CNS injuries, and can allow modulation of neurite ingrowth through the injury site in a long term manner.

In addition to CNS tissues, the collagen methacrylamides of the present invention can be used as a tissue scaffold for any collagen-based engineered or bio-artificial construct where 1) maintenance of the fibrillar nature of collagen is desired; 2) the mechanical properties of the collagen tissue/construct are sub-optimal and the strength and/or stiffness can be improved; 3) the bio-functionality of the collagen is sub-optimal and can be improved by attaching ligands to the collagen scaffold; 4) patterns of stiffness and/or biofunctional ligands are desired; and/or 5) the process can be done to cellular or acellular constructs.

For example, the collagen methacrylamides of the present invention can be used on a cell-compacted, collagen based blood vessel where the stiffness and strength of the vessel are improved via photocrosslinking. Cell-compacted vessel-equivalents, or bioartificial arteries are made by entrapping cells in a collagen network during fibrillogenesis. These cells compact or squeeze the gel into a tube-like structure around a slippery mandrel. However, these tubes traditionally lack the strength and stiffness on natural vessels without crosslinking. The cross-linking can usually be done chemically, which requires extensive incubation times (weeks) or enzymatically, which is prohibitively expensive. The photocrosslinking used in this invention only takes minutes.

Another use for collagen methacrylamides of the present invention is toward directing stem cell differentiation, the process by which stem cells differentiate into diverse specialized cell types. The microenvironment surrounding a stem cell, including the mechanical and bio-chemical properties of the extracellular matrix, has a profound effect on the proliferation rate of stem cells as well as differentiation fate.

For example, human mesenchymal stem cells (hMSC) differentiate into functional neuronal lineages, and the mechanical properties of the matrix are directly and solely responsible for the resultant differentiation fate. It has been demonstrated that hMSC differentiation on 2D substrates is determined by substrate stiffness. Substrate stiffness of 0.1-1 kPa, 8-17 kPa, or 25-40 k Pa results in neurogenic, myogenic, or osteogenic lineages, respectively. Additionally, the combination of substrate stiffness and the presentation of adhesive ligands may act synergistically to drive hMSC differentiation. For instance, hMSC differentiation can be pushed towards an osteogenic lineage via a stiff (80 kPa) substrate coated with type-I collagen, but type IV collagen on the same substrate results in differentiation into a myogenic lineage.

The collagen methacrylamides of the present invention thus can be used to investigate the effects of both bulk and localized modulation of substrate stiffness, as well as to determine whether patterned grafting of neurotrophic cues can be used to locally promote differentiation into a particular neuroectodermal lineage.

The following non-limiting examples set forth hereinbelow illustrate certain aspects of the invention.

EXAMPLES

Data was analyzed for statistical significance using a one-way ANOVA, significance level P<0.05, and the Turkey post hoc test for pair-wise comparisons (Kaleidagraph v4.1, Synergy Software, Reading, Pa.).

Example 1

Synthesis of Methacrylate-Derivatized Type-I Collagen

Type I bovine collagen was modified by replacing free amines with methacrylate groups to create collagen methacrylamide (CMA). 1-ethyl-3-(3-dimethylaminopropyl) carbodiimide) (EDC) and N-hydroxysuccinimide (NHS) in MES buffer were used to activate the carboxyl group of methacrylic acid (MA) for 10 minutes at 37° C., which was added to the collagen (3.75 mg/mL) in 0.02N acetic acid and reacted for 24 hours at 4° C. Following the reaction, the CMA was dialyzed against 0.02N acetic acid, lyophilized for 72 hours, and finally re-suspended in 0.02N acetic. Derivatization was verified using $H^1$ NMR. NMR spectra were obtained with a Bruker Avance 360 MHz NMR Lyophilized CMA was dissolved in deuterated DMSO (10 mg/mL) overnight and NMR spectra were calibrated to the residual solvent peak (2.50 ppm). Derivatization efficiency was also evaluated using a trinitrobenzenesulfonic acid (TNBSA) assay, modified from Sheu et al to quantify the free amines present before and after derivatization. (Sheu et al., "Characterization of Collagen Gel Solutions and Collagen Matrices for Cell Culture," *Biomater.*, 22(13), 1713-1719 (2001).)

Figure 4:
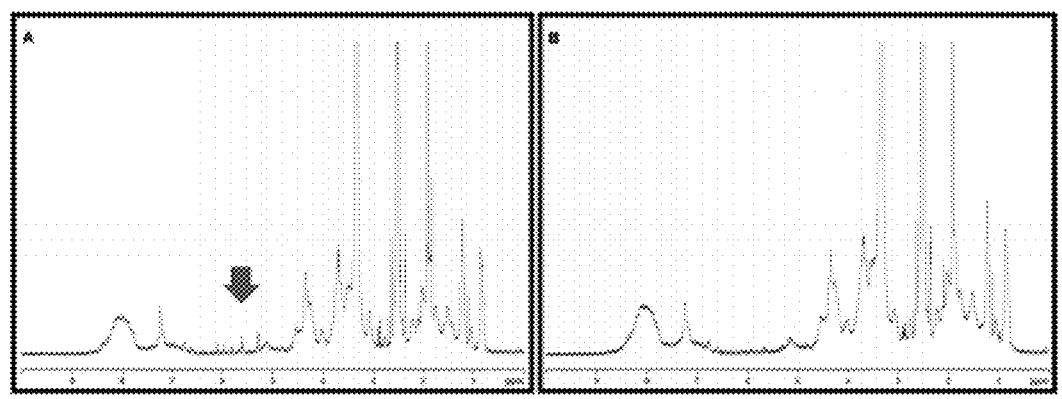
FIG. 4. depicts the $^1H$ NMR spectra of CMA and Native Type I collagen.

Proton NMR showed large peaks at 5.3 and 5.6 ppm, indicating that methacrylate derivatization of free amines was successful. Additional smaller peaks near 6 ppm suggested that derivatization of other less prevalent reactive side groups occurred as well, as shown in FIG. 4a. NMR spectra are other otherwise nearly identical to native collagen, verifying that no other significant reactions occurred during the synthesis and purification process, as shown in FIG. 4b. Quantification of free amines using TNBSA showed that approximately 20% of the free amines were converted to methacrylamide groups This method produced functional methacrylation of collagen as seen by reactivity to photocrosslinking in rheometry experiments, while largely preserving the natural structure of collagen, evidenced by the ability of CMA to self-assemble when alkalinized.

Example 2

Optimization of the Synthesis of Methacrylate-Derivatized Type-I Collagen

An additional step for optimizing derivatization efficiency is discussed herein. The initial methacrylation step targets the free amines on collagen, of which there are approximately 164 per triple helical type-I collagen molecule consisting of two α chains and one β chain. While this number of potential grafting sites is large enough to allow a functional modification of collagen, when more methacrylate groups are be added, the CMA is a more robust material in terms of the range of material properties achieved through photocrosslinking.

Another site of potentially graftable residues is on the carboxyl group present on the amino acids glutamate and aspartate, of which there are a combined 387 per triple helical collagen molecule. After the free amines on collagen have been converted into methacrylamides, a second round of EDC functionalization targeting the free carboxyls is done to prevent the collagen crosslinking to itself and rendering the material an unusable gelatinous mass during the reaction. Briefly, after derivatization of native collagen with methacrylic acid and dialysis of the excess reagents, the resultant CMA can then be further derivatized using aminoethylmethacrylate (AEM), which will form amide bonds with the EDC/sulfoNHS-activated carboxylic acid groups on collagen, as shown in FIG. 1. The resulting material, dubbed CMAx2, has over 3 times the number of photocross-linkable groups than the first generation CMA. Initial rheometry experiments show promising results, with auto-cross-linked CMAx2 having a storage modulus ~3 times higher than un-cross-linked CMAx2. The storage modulus increase is a significant improvement over the roughly 2-fold increase in storage modulus achieved by auto-cross-linking first generation CMA.

Example 3

Characterization of Mechanical Properties of Hybrid Hydrogels

UV rheometry was used to evaluate changes in bulk mechanical properties of collagen gels as a result of methacrylation and UV-mediated crosslinking. Currently, a repeatable methodology for performing rheometry experiments on CMA, CMAx2 and native collagen hydrogel samples has been developed and implemented.

To evaluate the changes in mechanical properties, CMA was mixed in 1 mL batches, in which 677 μL CMA (3.75 mg/mL) was added to 20 μL HEPES, 140-μL 0.15N NaOH, 100 μL 10×PBS, 53 μL PBS, and 10 μL of a photoinitiator solution containing 2.5% (w/v) Irgacure 2959 (I2959) in methanol. This collagen solution was immediately loaded between a 20 mm top parallel plate and a quartz lower plate on a modified Kinexus Ultra rotational rheometer (Malvern Instruments). The temperature was raised to 37° C. with a Peltier-controlled stage to induce fibrillogenesis. After 10 mins. the sample was exposed to UV light (365 nm, 100 mW/cm$^2$) through the quartz bottom plate for 90 seconds to photocross-link the gel. Throughout this process, and continuing for 20 min, the sample was oscillated (0.5% strain, 1 rad/s), and the resultant torque was measured to obtain mechanical properties of the material during self-assembly and photocrosslinking.

Figure 5:
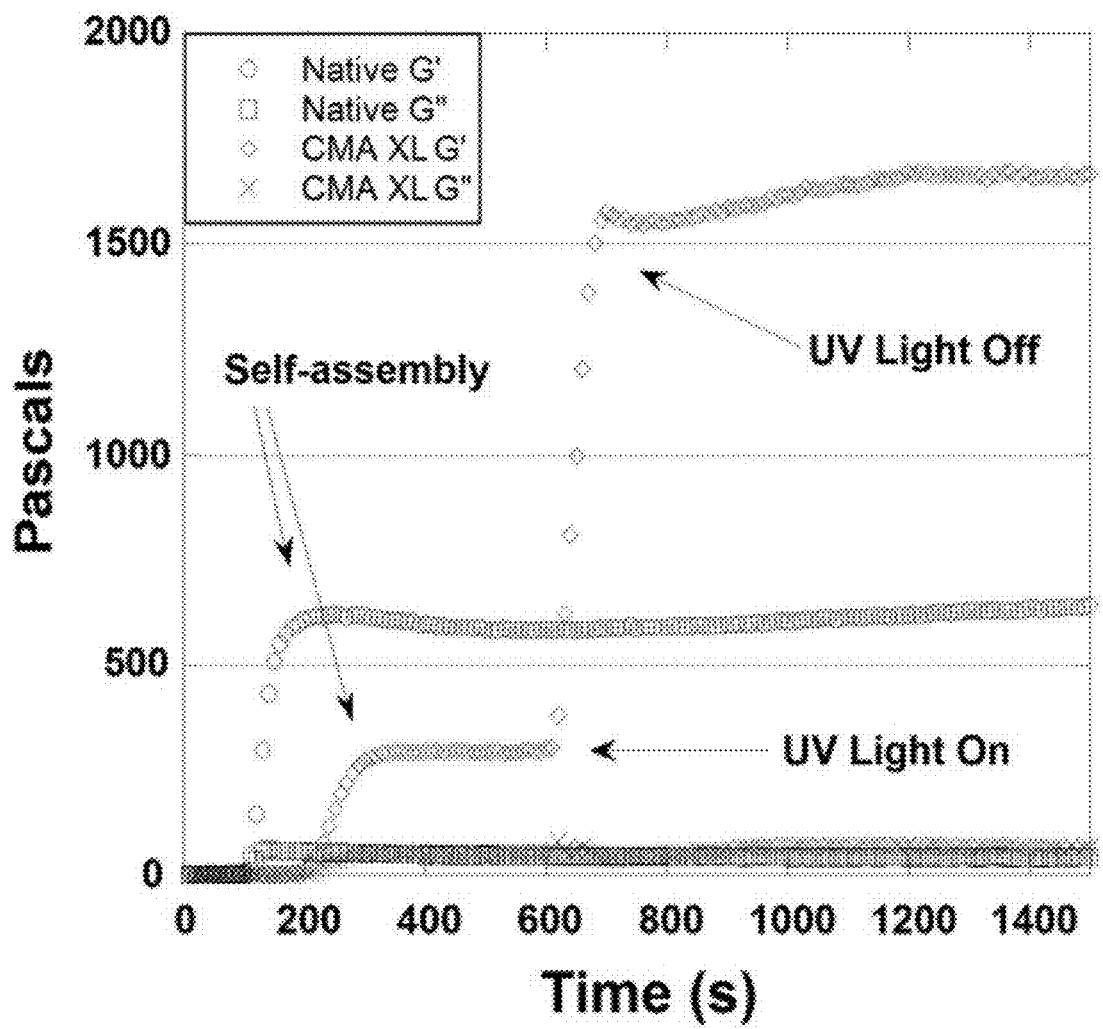
FIG. 5 depicts real-time rheological data of native collagen (○G', □G") and CMA (◇G', X G") during self-assembly and photocross-linking.
Figure 6:
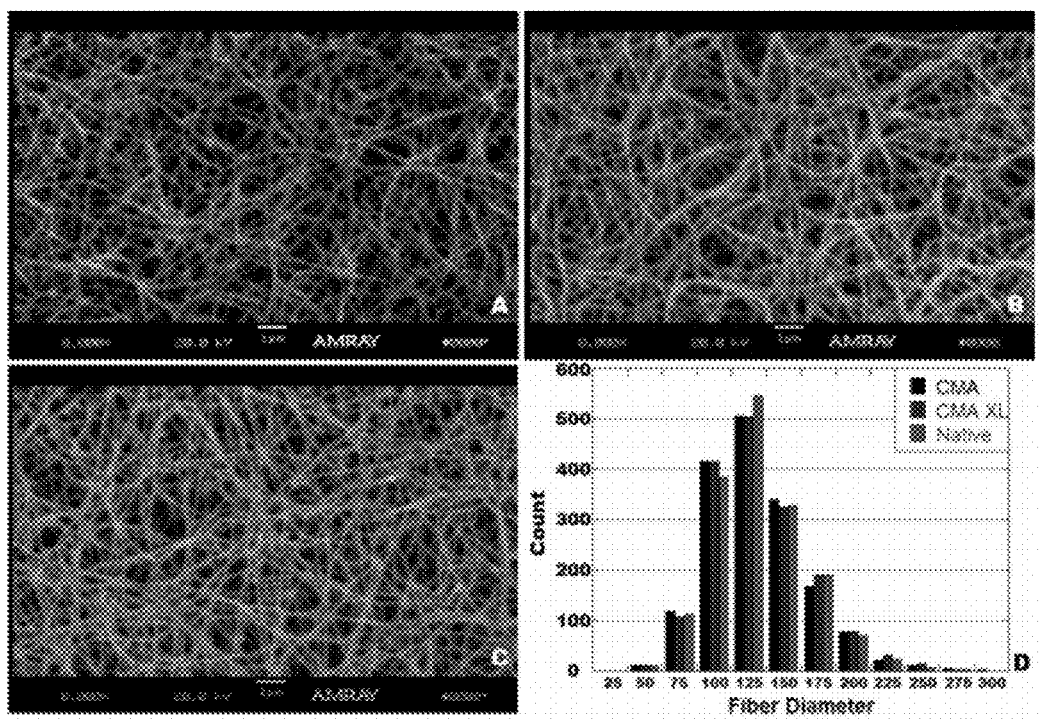
FIG. 6 depicts SEM images of (A) CMA, (B) Photocross-linked CMA, and (C) native collagen. Images are 8000×, scale bar=1 μm. Histogram (D) shows diameter distribution in 25 nm bins.

Rheological analysis (FIG. 5) of CMA gels showed that the material is capable of self assembly similar to native collagen, as evidenced by the increase is storage modulus around 150-300 seconds after incubation at 37° C. Photolabile functionality of CMA was demonstrated by the rapid, five-fold increase in storage modulus (G') upon irradiation with UV light. A small, oscillatory increase in the loss modulus (G") was seen during irradiation, however once the light source was turned off after 60 s the equilibrium loss modulus was slightly lower than prior to photocrosslinking. The large increase in storage modulus from pre-crosslinked (323.4±7.8 Pa at t=600 s) to post-crosslinked (1316.8±51.3 Pa at t=1200 s) along with the slight decrease in loss modulus (57.7±4 Pa to 39.8±6.5 Pa) indicated that photocrosslinking of CMA results in a mechanically stiffer and more elastic material.

Example 4

Cytocompatibility and Cytotoxicity Studies

Adult human mesenchymal stem cells (hMSC) were expanded in tissue culture flasks for 7 days in α-MEM (Gibco) supplemented with 20% FBS (Atlanta Biologicals), 1% penicillin and streptomycin (Sigma-Aldrich), and 2 ng/mL bFGF (Peprotech). Following expansion, hMSC were detached via trypsin/EDTA, washed in culture media, and encapsulated within CMA gels containing 0.025% I2959. Gels were exposed to UV for 90 seconds, and returned to culture for 24 hours. Viability was assessed by staining with Hoechst 33342, Calcein-AM, and ethidium homodimer. Fluorescent microscopy was used to estimate percent viability based on intercellular cleavage of calcein-AM to calcein (live) or uptake of ethidium into the nucleus (dead). Hoechst 33342 was used to visualize nuclei.

Cytotoxicity studies show that the photocrosslinking process can occur in the presence of entrapped hMSC. Twenty-four hours following exposure to UV light in the presence of photo-initiator, the majority of cells were positive for calcein, which is only taken up by live cells. Only a small number of cells are positive for ethidium, which can only permeate dead cells with compromised cell membranes and fluoresces upon intercalation with DNA. Additional viability studies using MTS to measure mitochondrial activity show that hMSC are metabolically active following the photocrosslinking process with only a minimal reduction in mitochondrial activity.

Example 5

Effect of Derivatization Reaction and Photocrosslinking Process on the Degradation of the Gels Degradation of the mechanical properties of gels was evaluated via reduction in storage modulus (G') due to enzymatic cleavage of collagen fibrils. For this rheological analysis during enzymatic degradation, collagen or CMA solutions were prepared as above and loaded onto the rheometer in a poly(dimethyl siloxane) (PDMS) ring, allowed to gel at 37° C., and exposed to UV for crosslinking. Samples were then cooled to 15° C. and Type-I collagenase (Sigma, 0.1 mg/mL) was added and allowed to diffuse into the gel for 5 minutes. After aspiration of excess collagenase, the upper parallel plate was lowered onto the gels, temperature was returned to 37° C., and the sample was exposed to 3 seconds of oscillatory shear (1 rad/s, 0.5% strain) every 5 minutes for 1 hour. Degradation of the fibrillar structure was evaluate with a separate assay, adapted from Daminik et al. (Damink et al., "In Vitro Degradation of Dermal Sheep Collagen Cross-Linked Using a Water-Soluble Carbodiimide," *Biomater.*, 17(7), 679-684 (1996).) Collagenase was added to gelled and photocrosslinked collagen and CMA in a 96 well plate, where samples of the gel supernatant were removed every 30 minutes and the total liberated protein determined by BCA assay.

Collagenase degradation assays were performed to assess whether the derivatization reaction or the photocross-linking process had an effect on enzymatic degradation of the gels. Rheological tests showed that the mechanical degradation rate, reported here as the reduction in storage modulus as a percentage of initial storage modulus over time, was not statistically different between native collagen and CMA, indicating similar degradation kinetics. However, the degradation rate of photocross-linked CMA was significantly lower (P<0.05) than both native collagen and CMA. A separate collagenase test analyzed the percent of protein liberated from the gels following 3 hours of exposure to collagenase, as determined by a BCA total protein assay. BCA data showed slightly different results, namely that native collagen was most liberated after 3 hours, followed by CMA, with photocross-linked CMA least degraded.

Additionally, collagenase degradation assays were performed to determine if the methacrylate derivatization had any effect on the enzymatic degradation of the fibrillar gels both before and after crosslinking. Since type-I collagenase requires an intact triple helix to effectively degrade fibrillar collagen, if the tertiary structure was indeed altered significantly then collagenase degradation rates should also be affected, which may affect the biodegradability of the material as well as the extent that cells may remodel the scaffold. (Walton et al., "Influence of Telopeptides, Fibrils and Cross-Linking on Physicochemical Properties of Type I Collagen Films," *J. Mater. Sci.-Maters. in Med.*, 21(2), 451-461 (2010).) Also, cross-linking of collagen has previously been shown to decrease the collagenolytic degradation rate, as crosslinks between collagen molecules necessarily increases the number of ligations necessary to liberate protein fragments as well as affecting the availability of recognizable triple helical segments. (Weadock et al., "Effect of Physical Cross-Linking Methods on Collagen-Fiber Durability in Proteolytic Solutions," *J. Biomed. Mater. Res.*, 32(2), 221-226 (1996); Park et al., "Characterization of porous collagen/hyaluronic acid scaffold modified by 1-ethyl-3-(3-dimethylaminopropyl)carbodiimide cross-linking," *Biomater.*, 23(4), 1205-1212 (2002).)

Two different assays were used to evaluate the mechanical degradation as well as the chemical degradation of pre- and post-photocrosslinked CMA gels as compared to native collagen. Rheological testing was performed to evaluate the percent reduction in initial storage modulus over time during a continuous two hour test. Chemical degradation was assessed via sampling collagenase-exposed gels over a three hour period. Rheological tests showed that the mechanical degradation rate was not statistically significant between native and un-cross-linked CMA gels, while photo-cross-linked CMA gels showed a significantly lower degradation rate (P<0.05). Conversely, the chemical degradation assay indicated that significantly more protein was liberated from native collagen gels as compared to uncrosslinked CMA gels, and crosslinked CMA was significantly less degraded than both native and un-cross-linked gels after three hours.

This apparent discrepancy between the rheological and chemical assays may be possibly attributed to the previously mentioned issue of ectopic crosslinks that result in anomalous structure formation during fibrillogenesis. These non-helical structures may not be readily degraded by collagenase due to the lack of helical structure as well as stabilizing covalent bonds. Thus, they are not liberated into solution, as seen by the BSA assay, while also not contributing to the mechanical strength of the gels, and as such their lack of degradation has not effect on the storage modulus during the rheological collagenase degradation assay. In both assays, as expected, the photocross-linked CMA was significantly less degradable, although it still showed noticeable enzymatic degradability. This aspect may prove extremely useful, as photocross-linking may be exploited to spatially control the degradation rate of individual regions of the scaffold.

Example 6

SEM Analysis

Native collagen and CMA gels were prepared as above, except on glass coverslips. Following self-assembly and photocrosslinking, gels were dehydrated in a series of aqueous acetone solutions (25%, 50%, 75%, 95%, 100%) and critical point dried. Samples were then sputter coated with gold/palladium and imaged via SEM (Amray). Fiber diameter was sampled on a grid and measured using ImageJ (ImageJ, NIH, Bethesda Md.).

Qualitative analysis of SEM images showed no apparent differences in fibril size, orientation, or quantity between native collagen and CMA, as shown in FIGS. 11A and B, further indicating that the methacrylation reaction largely preserves the quaternary structure of the collagen. Similar analysis of photocross-linked CMA, shown in FIG. 11C, showed no differences, indicating that the photocrosslinking process does not significantly alter the fibrillar ultrastructure. Quantification of fiber diameter, shown in FIG. 11, confirmed that there was no statistical difference in average fiber diameter or fiber size distribution.

Example 7

Hybrid-Hydrogel Formation, Cross-Linking & Mechanical Testing

Formation of the CMA-PEG hybrid-hydrogel was completed as follows. 800 µl cylindrical gels of alkalinized CMA, both with and without PEG diacrylate (0.1% w/v), were formed in poly(dimethyl siloxane) (PDMS) molds on glass slides and allowed to self assemble into stable gels. The stable gels of alkalinized CMA, both with and without PEG diacrylate, were then crosslinked with 0.1% Irgacure 2959 (I2959) and a 5 minute exposure to UV light (365 nm), and loaded on to a Kinexus Ultra rotational rheometer in parallel plate mode at 37° C. A strain controlled (2%) frequency sweep (0.1-10 rad/s) was employed to characterize the storage and loss moduli of the material at various strain rates.

Discussion

Rotational rheometry is used to evaluate changes in bulk mechanical properties of collagen gels as a result of methacrylation and UV-mediated crosslinking. Currently, a repeatable methodology for performing rheometry experiments on CMA and native collagen hydrogel samples has been developed and implemented. Briefly, small volume gels (approximately about 600 µL-about 800 µL) are cast into cylindrical PDMS molds on glass slides to create thin cylindrical gels. After self-assembly, gels are crosslinked in situ, and then hydrated with PBS. The entire construct is loaded onto the rheometer by securing the glass slide to the lower parallel plate of the rheometer with vacuum grease. This methodology removes the variability seen due to manual manipulation of gels during the loading process. The manual manipulation creates artifacts when attempting to characterize gels of very low or very high stiffness. This methodology produces consistent data that represents the hydrogels' true material properties.

With regard to the instant invention, rheometry experiments show a significant increase in stiffness after photocrosslinking. Control sample experiments including native collagen, uncross-linked CMA, UV-alone treated collagen and CMA, and chemically crosslinked collagen demonstrate the role of CMA functionality in mechanical property modulation. CMA macromer concentration experiments show that within the range of 2-3.5 mg/ml the increase in stiffness achieved via photocrosslinking is linear in terms of fold-increase of storage modulus. Initial material properties of CMA gels can be controlled by changing the macromer concentration.

Rheological studies of CMA-PEG cross-linking using 0.1% (w/v) PEG258DA show a large increase in storage modulus, while similar studies with PEG of Mw 1,500 Da and 2,000 Da do not show the same effect at 0.1% (w/v). This is somewhat expected due to the smaller quantity of functional acrylate groups per unit mass. However, even with 1% (w/v) of PEG of 2,000 Da, there is no measurable increase in the storage modulus as compared to autocrosslinked CMA. Thus, CMA can autocrosslink, and additional stiffness can be achieved through the use of PEG crossbridges, namely PEG used with a molecular weight of 258 Da.

Thus, following photocrosslinking, the storage modulus of the crosslinked CMA is two-fold higher than that of native collagen at the same concentration. However, the storage modulus of un-cross-linked CMA hydrogels is slightly lower than that of native collagen, presumably due to unwanted cross-linking of collagen molecules during the synthesis reaction.

This is consistent with SEM images, as fibril diameter and distribution are essentially identical between native collagen and CMA. However, there are occasional rosette-like structures within the CMA gels due to multiple branching incidents during self-assembly, which can be a result of multiple collagen molecules being crosslinked during the CMA synthesis reaction. These rosettes may disrupt the local mechanical properties of the gels by forming small discontinuities within the fibrous network that may be prone to microscopic tears, thus resulting in a lower bulk storage modulus. This reduction in bulk material properties is of little concern, as the un-cross-linked modulus can be controlled via the CMA concentration.

The cytocompatibility and cytotoxicity studies show that methacrylate derivatization has no apparent impact on cellular compatibility, as evidenced by the maintenance of viability and normal morphology of hMSC entrapped and cultured within CMA gels. Previous studies have shown that the photoinitiator used here, I2959, is generally well tolerated at the concentrations used, although some cell types are more susceptible than others In the inventive method, the photocrosslinking process is well tolerated by hMSC, as no apparent increase in ethidium-positive cells is observed 24 hours after photocrosslinking as compared to cells in native collagen gels.

Furthermore, mitochondrial viability is not significantly disturbed by exposure to photocrosslinking conditions. This observation of minimal detriment from photocrosslinking is encouraging, as it demonstrates that modulation of CMA scaffolds can be conducted in the presence of encapsulated cells, allowing for in situ modification of these injectable cellularized scaffolds. The localized effects of in situ photocrosslinking on hMSC differentiation allows recapitulation of the mechanical composition of native CNS tissues as evidenced by the range of stiffness available via degree of crosslinking. By taking advantage of the spatial control provided by the instant invention, complex 3-dimensional hydrogel scaffolds that have non-homogenous microenvironments are created. As actual tissues are comprised of complex mixtures of cell types and matrices, this material allows for highly controllable scaffolds capable of directing a single stem cell population into differentiation along multiple lineage pathways simultaneously.

The foregoing examples and descriptions of the preferred embodiments should be taken as illustrating, rather than limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

All references cited herein are incorporated by reference herein in their entireties.

What is claimed is:

1. A method of synthesizing a methacrylate-derivatized type-I collagen, comprising:
   (a) reacting methacrylic acid with a carboxylic acid activating reagent in the presence of a carbodiimide to form a methacrylic acid with an activated carboxylic acid group; and
   (b) reacting free amino groups on a type-I collagen with the activated carboxylic acid groups on said methacrylic acid to form a collagen methacrylamide;
   (c) removing excess reagents from said collagen methacrylamide;
   (d) reacting free carboxylic acid groups on said collagen methacrylamide with a carboxylic acid activating reagent in the presence of a carbodiimide to form a collagen methacrylamide with activated carboxylic acid groups; and
   (e) reacting said activated carboxylic acid groups on said collagen methacrylamide with aminoethylmethacrylate in the presence of a carbodiimide to form a collagen methacrylamide amidoethylmethacrylate.

2. The method of claim 1, wherein said carbodiimide is selected from the group consisting of 1-ethyl-3-(3-dimethylamino-propyl) carbodiimide (EDC), N,N'-dicyclohexylcarbodiimide (DHC), N,N'-diisopropylcarbodiimide (DIC), 1-(3-dimethylaminopropyl)-3-ethyl carbodiimide hydrochloride, N-cyclohexyl-N'-(2'-morpholinoethyl) carbodiimide-metho-p-toluene sulfonate, N-benzyl-N'-(3'dimethylaminopropyl-carbodiimide hydrochloride, 1-ethyl-3-(3-dimethyl-aminopropyl)carbodiimide methiodide and N-ethylcarbodiimide hydrochloride.

3. The method of claim 2, wherein said carbodiimide is EDC.

4. The method of claim 1, wherein said carboxylic acid activating reagent is selected from the group consisting of N-hydroxysuccinimide (NHS), N-hydroxysulfosuccinimide (Sulfo-NHS), Hydroxybenzotriazole (HOBt), 1-Hydroxy-7-azabenzotriazole (HOAt) and pentafluorophenol.

5. The method of claim 4, wherein each carboxylic acid activating reagent is NHS.

6. A collagen methacrylamide, prepared by a method comprising:

(a) reacting methacrylic acid with a carboxylic acid activating reagent in the presence of a carbodiimide to form a methacrylic acid with an activated carboxylic acid group; and
(b) reacting free amino groups on a type-I collagen with the activated carboxylic acid groups on said methacrylic acid to form a collagen methacrylamide;
wherein between about 5 and about 25% of the collagen free amino groups are acrylate-functionalized.

7. A cross-linked collagen comprising the collagen methacrylamide of claim 1.

8. The cross-linked collagen of claim 7, wherein a portion of the acrylate functional groups of said methacrylamide are cross-linked with a poly(alkylene oxide) dimethacrylate.

9. The cross-linked collagen of claim 8 wherein said poly(alkylene oxide) dimethacrylate is a poly(ethylene glycol) dimethacrylate.

10. The cross-linked collagen of claim 7, characterized in that it is lyophilized.

11. The cross-linked collagen of claim 7, characterized in that it is in the form of a hydrogel.

12. A wound dressing comprising the cross-linked collagen of claim 7.

13. A tissue replacement material for reconstructive or cosmetic surgery comprising the cross-linked collagen of claim 7.

14. The tissue replacement material of claim 13, characterized in that it is configured or constructed to replace skin bone tissue, a blood vessel, fascia, connective tissue or a ligament.

15. A dermal filler for cosmetic surgery comprising the cross-linked collagen of claim 7.

16. A bone tiller for reconstructive surgery comprising the cross-linked collagen of claim 7.

17. An artificial skin or skin replacement material for burn treatment or wound healing comprising the cross-linked collagen of claim 7.

18. A scaffold for tissue engineering comprising the cross-linked collagen of claim 7.

19. An implantable medical device comprising the cross-linked collagen claim 7.

20. The collagen methacrylamide of claim 6, characterized in that it is lyophilized.

21. The collagen methacrylamide of claim 6, characterized in that it is a hydrogel.

22. A tissue replacement material for reconstructive or cosmetic surgery comprising the collagen methacrylamide of claim 6.

23. An implantable medical device comprising the collagen methacrylamide of claim 6.

* * * * *